(12) United States Patent
Washburn et al.

(10) Patent No.: US 11,643,375 B2
(45) Date of Patent: May 9, 2023

(54) PROCESSES FOR CONVERTING BENZENE AND/OR TOLUENE VIA METHYLATION

(71) Applicant: ExxonMobil Chemical Patents Inc., Baytown, TX (US)

(72) Inventors: Seth M. Washburn, Houston, TX (US); Hsu Chiang, Humble, TX (US); Tan-Jen Chen, Seattle, WA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/433,040

(22) PCT Filed: Mar. 18, 2020

(86) PCT No.: PCT/US2020/023418
§ 371 (c)(1),
(2) Date: Aug. 23, 2021

(87) PCT Pub. No.: WO2020/197893
PCT Pub. Date: Oct. 1, 2020

(65) Prior Publication Data
US 2022/0153660 A1    May 19, 2022

Related U.S. Application Data

(60) Provisional application No. 62/825,613, filed on Mar. 28, 2019.

(30) Foreign Application Priority Data

Jul. 11, 2019 (EP) ..................................... 19185754

(51) Int. Cl.
*C07C 2/86* (2006.01)
*B01J 29/70* (2006.01)

(52) U.S. Cl.
CPC ........... *C07C 2/865* (2013.01); *B01J 29/7038* (2013.01); *C07C 2/864* (2013.01); *C07C 2529/70* (2013.01)

(58) Field of Classification Search
None
See application file for complete search history.

(56) References Cited

U.S. PATENT DOCUMENTS

| 4,112,008 A | 9/1978 | Marcilly |
| 6,506,954 B1 * | 1/2003 | Brown .................... C07C 15/08 585/634 |

(Continued)

FOREIGN PATENT DOCUMENTS

CN    104096589 A    10/2014

OTHER PUBLICATIONS

U.S. Appl. No. 17/431,846, filed Aug. 18, 2021 entitled "Processes and Systems for Converting Benzene and/or Toluene via Methylation" Inventors: Seth et al.

(Continued)

*Primary Examiner* — Ali Z Fadhel

(57) ABSTRACT

This disclosure provides improved processes for converting benzene/toluene via methylation with methanol/dimethyl ether for producing, e.g., p-xylene. In an embodiment, a process comprises contacting a methylation agent feed with an aromatic hydrocarbon feed in the presence of a methylation catalyst in a methylation reactor at increased pressure. Reduced methylation catalyst deactivation can be achieved with increased pressure in the methylation reactor.

27 Claims, 2 Drawing Sheets

(56) References Cited

U.S. PATENT DOCUMENTS

| | | | |
|---|---|---|---|
| 9,006,506 B2* | 4/2015 | Zheng | C07C 2/865 |
| | | | 585/446 |
| 9,440,893 B2 | 9/2016 | Helton et al. | |
| 9,783,462 B2 | 10/2017 | Ghosh et al. | |
| 2013/0253245 A1* | 9/2013 | Zheng | C07C 2/864 |
| | | | 585/467 |
| 2014/0100402 A1* | 4/2014 | Gawlik | C07C 7/005 |
| | | | 585/446 |
| 2017/0240487 A1 | 8/2017 | Tinger et al. | |
| 2018/0099913 A1 | 4/2018 | Chen et al. | |
| 2018/0170828 A1 | 6/2018 | Schmidt et al. | |
| 2018/0170831 A1* | 6/2018 | Jan | C07C 2/864 |
| 2018/0170841 A1 | 6/2018 | Schmidt et al. | |
| 2018/0170842 A1 | 6/2018 | Schmidt et al. | |

OTHER PUBLICATIONS

U.S. Appl. No. 17/431,745, filed Aug. 18, 2021 entitled "Processes for Converting Benzene and/or Toluene Via Methylation" Inventors: Seth et al.

U.S. Appl. No. 16/820,227, filed Mar. 16, 2020 entitled "Processes for Converting Aromatic Hydrocarbons Using Passivated Reactor" Inventors: Seth et al.

* cited by examiner

PROCESSES FOR CONVERTING BENZENE AND/OR TOLUENE VIA METHYLATION

CROSS-REFERENCE TO RELATED APPLICATIONS

This application is a US national phase application of PCT Application Serial No. PCT/US2020/023418 having a filing date of Mar. 18, 2020, which claims priority to and the benefit of U.S. Provisional Application No. 62/825,613 having a filing date of Mar. 28, 2019 and European Patent Application No. 19185754.9 having a filing date of Jul. 11, 2019, the disclosures of all of which are incorporated herein by reference in their entireties.

FIELD

This disclosure relates to processes and systems for converting benzene and/or toluene. In particular, this disclosure relates to processes and systems for converting benzene and/or toluene via methylation with methanol and/or dimethyl ether. This disclosure is useful, e.g., in making p-xylene and/or o-xylene via benzene/toluene methylation with methanol.

BACKGROUND 1,4-Dimethylbenzene (para-xylene, or p-xylene) is a valuable chemical feedstock and is used mainly for the production of terephthalic acid and polyethylene terephthalate resins, in order to provide synthetic textiles, bottles, and plastic materials among other industrial applications. As commercial applications of p-xylene have increased, there has been an increased need for more selective processes and increased yields for p-xylene production. Worldwide production capacity of p-xylene is about 40 million tons per year, and the continually increasing demand for purified terephthalic acid in polyester production processes is projected to provide a corresponding demand to the p-xylene market. Thus, there has been a corresponding increase in demand for the development of efficient and cost-effective p-xylene formation and isolation processes.

p-Xylene can be extracted from the BTX aromatics (benzene, toluene and xylene isomers) in the catalytic reformate produced by catalytic reforming of petroleum naphtha. Alternatively, p-xylene can be produced via toluene disproportionation, toluene transalkylation with C9+ aromatics, or toluene methylation with methanol. Regardless of the method of production, p-xylene is then separated out in a series of distillation, adsorption, crystallization and reaction processes from other C8 aromatic isomers, such as meta-xylene, ortho-xylene, and ethylbenzene. The melting point of p-xylene is the highest among such series of isomers, but simple crystallization does not allow easy purification due to the formation of eutectic mixtures. Consequently, current technologies for p-xylene production are energy intensive, and p-xylene separation and purification are a major cost factor in the production of p-xylene. Hence, alternative methods to selectively produce p-xylene are still needed.

The methylation of toluene and/or benzene is a favored route to the formation of p-xylene because of the low cost of starting materials and the potential to provide high yields. One methylation method uses methanol as a methylating agent. Most of the work related to alkylation with methanol has concentrated on using selectivated zeolite catalysts, such as steamed phosphorous-containing ZSM-5 (U.S. Pat. Nos. 9,440,893B2 and 9,783,462B2), to increase the p-xylene selectivity in the methylation reaction. A result of using such shape selective catalysts is the need to operate at fairly high temperatures (approx. 500-600° C. or higher), which, in turn, causes rapid catalyst deactivation, significant light gas generation through methanol to olefin chemistry, and production of other trace by-products that have to be removed from the product. In the high temperature process using such selectivated catalysts, essentially all of the methanol can be consumed.

With the growing need for p-xylene there is greater demand for cost effective and efficient synthesis and isolation of p-xylene. One way to increase efficiency and decrease cost would be to suppress catalyst deactivation. The catalyst deactivation rate can affect not only the type of reactor deployed but the cycle time of the catalyst. A challenge that p-xylene manufacturers face is the high cost of catalyst regeneration and, to surmount that challenge, progress toward slowing or stopping catalyst deactivation is needed. Thus, there is a need to slow catalyst deactivation rates which in turn lowers the frequency of catalyst regeneration, and improves upon the production of xylenes.

1,2-Dimethylbenzene (ortho-xylene, or o-xylene) is another valuable chemical intermediate, with demand over the past two decades growing at about 2% per year. o-Xylene is used mainly for the production of phthalic anhydride, a common intermediate in production of plasticizers, dyes, and enteric coatings for pharmaceuticals. As commercial applications of o-xylene continue to increase, there is an increased need for more selective processes and increased yields for o-xylene production. The methylation of toluene can also produce o-xylene.

This disclosure satisfies these and other needs.

There is a need for suppression of catalyst deactivation in processes for the conversion of benzene and/or toluene via methylation to produce p-xylene.

References for citing in an Information Disclosure Statement ((37 C.F.R. 1.97(h)): U.S. Pub. Nos. 2018/0099913, 2018/0170828, 2018/0170831, 2018/0170841, and 2018/0170842.

SUMMARY

It has been found that conducting the methylation of benzene and/or toluene in the presence of a methylation catalyst such as zeolite at increased pressure, such as at an absolute pressure above 4300 kPa, one can achieve a significantly reduced catalyst deactivation rate of the methylation catalyst.

Thus, in a first aspect, this disclosure relates to a process for converting benzene and/or toluene, the process comprising: (a) feeding an aromatic hydrocarbon feed and a methylating agent feed into a methylation reactor, the aromatic hydrocarbon feed comprising benzene and/or toluene, and the methylating agent comprising methanol and/or dimethyl ether; and (b) contacting the aromatic hydrocarbon feed with the methylating agent feed in the presence of a methylation catalyst in the methylation reactor under methylation reaction conditions comprising an absolute pressure of at least 4300 kPa, to produce a methylation product mixture effluent comprising toluene, p-xylene, methanol, and dimethyl ether.

In a second aspect, this disclosure relates a process for converting benzene and/or toluene, the process comprising contacting an aromatic hydrocarbon feed and a methylating agent feed in a methylation reactor in the presence of a methylation catalyst under methylation reaction conditions to produce a methylation product mixture effluent, wherein the aromatic hydrocarbon feed comprises benzene and/or toluene, the methylating agent feed comprises methanol and/or dimethyl ether, and the methylation conditions comprise an absolute pressure of from 4650 kPa to 8500 kPa and a temperature of from 200 to 500° C.

In a third aspect, this disclosure relates to a process for converting for converting benzene and/or toluene, the process comprising: (a) feeding an aromatic hydrocarbon feed and a methylating agent feed into a methylation reactor, the aromatic hydrocarbon feed comprising benzene and/or toluene, and the methylating agent comprising methanol and/or dimethyl ether; (b) contacting the aromatic hydrocarbon feed with the methylating agent feed in the presence of a methylation catalyst in the methylation reactor under methylation reaction conditions comprising an absolute pressure in the methylation reactor of below 4300 kPa, to produce a methylation product mixture effluent comprising toluene, p-xylene, methanol, and dimethyl ether; and (c) increasing the absolute pressure in the methylation reactor to at least 4200 kPa.

DETAILED DESCRIPTION

Figure 1:
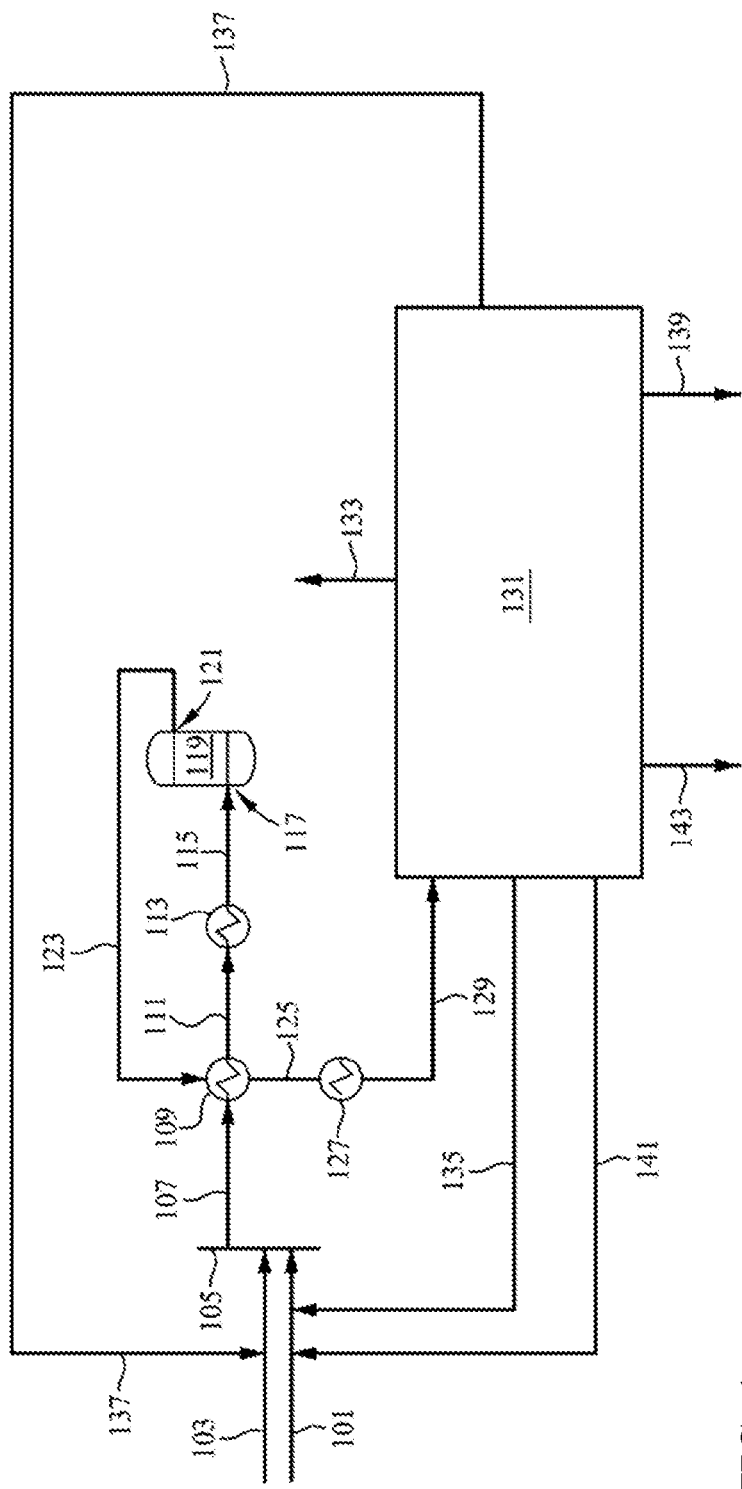
FIG. 1 is a schematic diagram illustrating a process for converting toluene/benzene via methylation with methanol to produce p-xylene, according to an embodiment of this disclosure.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments producing "a xylene" include embodiments where one, two or more xylenes are produced, unless specified to the contrary or the context clearly indicates that only one xylene is produced.

For the purposes of this disclosure, the nomenclature of elements is pursuant to the version of Periodic Table of Elements as described in CHEMICAL AND ENGINEERING NEWS, 63(5), pg. 27 (1985).

The following abbreviations may be used herein for the sake of brevity: RT is room temperature (and is 23° C. unless otherwise indicated), kPag is kilopascal gauge, psig is pound-force per square inch gauge, psia is pounds per square inch absolute, and WHSV is weight hourly space velocity. Abbreviations for atoms are as given in the periodic table (Al=aluminum, for example).

The term "conversion" refers to the degree to which a given reactant in a particular reaction (e.g., methylation, isomerization, etc.) is converted to products. Thus 100% conversion of toluene to xylene in a methylation refers to complete consumption of the toluene, and 0% conversion of the toluene refers to no measurable reaction of the toluene.

The term "selectivity" refers to the degree to which a particular reaction forms a specific product, rather than another product. For example, for the methylation of toluene, 50% selectivity for p-xylene means that 50% of the products formed are p-xylene, and 100% selectivity for p-xylene means that 100% of the product formed is p-xylene. The selectivity is based on the product formed, regardless of the conversion of the particular reaction.

"Alkylation" means a chemical reaction in which an alkyl group is transferred to an aromatic ring as a substitute group thereon from an alkyl group source compound. "Methylation" means alkylation in which the transferred alkyl group is a methyl. Thus, methylation of benzene can produce toluene, xylenes, trimethylbenzenes, and the like; and methylation of toluene can produce xylenes, trimethylbenzenes, and the like. Toluene methylation with methanol in the presence of a zeolite catalyst can be schematically illustrated as follows:

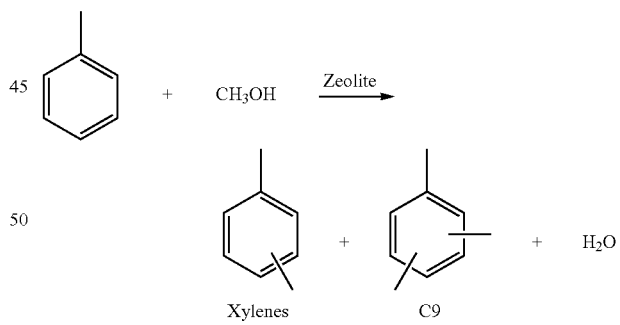

The xylenes include 1,2-dimethylbenzene (ortho-xylene, or o-xylene), 1,3-dimethylbenzene (meta-xylene, or m-xylene), and 1,4-dimethylbenzene (para-xylene, or p-xylene). One or more of these xylene isomers, particularly p-xylene and/or o-xylene, are high-value industrial chemicals. They can be separated to make corresponding products. The C9 hydrocarbons, though, are generally undesirable byproducts. The methylation reaction above can be performed in the presence of a methylation catalyst, such as a zeolite.

As used herein, the term "molecular sieve" means a substance having pores of molecular dimensions that only permit the passage of molecules below a certain size.

Examples of molecular sieves include but are not limited to zeolites, silicoaluminophosphate molecular sieves, and the like.

In this disclosure, unless specified otherwise or the context clearly indicates otherwise, "space hourly weight velocity" is based on the combined flow rate of the aromatic hydrocarbon feed and the methylating agent feed and the weight of the methylation catalyst.

This disclosure fulfils the need of effective and efficient processes for making p-xylene and/or o-xylene by toluene/benzene methylation with methanol, in which the catalyst exhibits a low deactivation rate. Toluene methylation processes of this disclosure utilize an increased pressure in the methylation reactor as compared to conventional methylation processes. The increased pressure significantly reduces the deactivation of the methylation catalyst under methylation conditions. Without being limited by theory, it is believed that catalyst deactivation may occur due to coke formation and one possible route by-product leading to coke formation is formaldehyde. Furthermore, without being limited by theory, it is believed that the increased pressure may cause the reaction to take place in the critical phase and that coke or coke precursors may be more soluble in that phase. The increased pressure may lead to less formaldehyde and coke formation or increased solubility and would therefore extend the life, and activity of a methylation catalyst.

Toluene methylation with methanol can be accomplished using MWW framework type zeolite catalysts at lower temperatures as compared to conventional methylation processes. The use of the MWW zeolite catalysts at lower temperature generates no to very little light gas or many of the other by-products. This has significant capital savings as separation and purification of the light gas (as well as other unwanted by-products generated at high temperature) is no longer needed. Furthermore, costs related to catalyst regeneration and energy consumption are decreased at the lower temperature thereby decreasing operation costs.

Methylation processes utilizing higher pressure in the methylation reactor can produce xylenes with less catalyst deactivation than previous processes conducted at a lower absolute pressure. In the present disclosure, an aromatic hydrocarbon feed is contacted with a methylating agent feed in a methylation reactor in the presence of a methylation catalyst under methylation conditions comprising an absolute pressure of at least 4300 kPa, to produce a methylation product mixture effluent comprising p- xylene. The process is effective to convert the benzene and/or toluene to xylenes with low catalyst deactivation resulting in substantial advantages including increased catalyst lifespan and therefore, lower production costs.

The selectivity to xylenes in the process can be on the order of 80%, with the main by-products being benzene and C9+ aromatics. The benzene and/or toluene can be separated from the methylation product mixture effluent and recycled back to the methylation reactor(s), while the C9+ aromatics can be separated for blending into the gasoline pool or transalkylated with additional benzene and/or toluene to make additional xylenes. The life of the methylation catalyst is enhanced as compared with existing processes because the increased pressure lowers deactivation rates. Moreover, the use of increased pressure may provide further advantages to a lower temperature benzene and/or toluene conversion process using large pore molecular sieves as the methylation catalyst, advantages over small or medium pore molecular sieves may include one or more of: (i) greater diffusion limits that allow the alkylation to be carried out at commercially viable weight hourly space velocities (WHSVs), (ii) lower methanol degradation at lower temperatures, (iii) little or no light gas production which allows easier and less costly purification, (iv) high selectivity to the para-isomer, and (v) higher weight hourly space velocities (WHSVs) than allowed with smaller pore molecular sieves.

Process for Converting Benzene and/or Toluene Via Methylation

The feeds to the present process include an aromatic hydrocarbon feed, comprising benzene and/or toluene, and a methylating agent feed comprising methanol and/or dimethyl ether. Any suitable refinery aromatic feed can be used as the source of the benzene and/or toluene. In some embodiments, the aromatic hydrocarbon feed comprises toluene at a concentration ≥90 wt % (e.g., ≥92 wt %, ≥94 wt %, ≥95 wt %, ≥96 wt %, ≥98 wt %, or even ≥99 wt %), based on the total weight of the aromatic hydrocarbon feed. In some embodiments, the aromatic hydrocarbon feed may be pre-treated to remove catalyst poisons, such as nitrogen and sulfur-compounds. The aromatic hydrocarbon feed may be fed as a single or multiple streams with the same or different compositions into the methylation reactor via one or more feed inlets. The methylating agent feed may be fed as a single or multiple streams with the same or different compositions into the methylation reactor via one or more feed inlets. Alternatively or additionally, at least a portion of the aromatic feed and at least a portion of the methylating agent feed may be combined and then fed into the methylation reactor as a single or multiple stream(s) via one or more inlets.

The methylation processes of this disclosure can be advantageously conducted at relatively high methylation reactor pressures. Operating pressures in the methylation reactor can vary with temperature but in some embodiments are ≥4200 kPa, such as ≥4300 kPa, ≥4400 kPa, ≥4500 kPa, ≥4600 kPa, ≥4650 kPa, ≥4700 kPa, ≥4800 kPa, ≥4900 kPa, ≥5000 kPa, ≥5250 kPa, ≥5500 kPa, ≥5750 kPa, ≥6000 kPa, or ≥6500 kPa, to ≤8500 kPa, such as ≤8000 kPa, ≤7500 kPa, ≤7000 kPa or ≤6000 kPa. For example, operating pressures may range from 4650 kPa to 8500 kPa, such as from 4650 kPa to 7000 kPa, or from 4650 kPa to 6000 kPa. In at least one embodiment, the combination of a high pressure (e.g., a pressure from 4650 kPa to 8500 kPa, such as from 4650 kPa to 6000 kPa) and a low temperature (e.g., a temperature from 250° C. to 500° C.), decreases the amount of light gases produced in the methylation reaction, and may also decrease the catalyst aging rate.

In some embodiments the operating pressure in the methylation reactor can be increased over time. The reactor pressure may be increased in direct proportion to the catalyst deactivation rate or WHSV. In some embodiments the operating pressure is increased for a period of time and then held constant, for example increased from 4300 kPa at a certain rate until reaching a pressure of 4650 kPa and then held at 4650 kPa.

The methylation process of this disclosure can be advantageously conducted at relatively low methylation reactor temperatures, for example ≤500° C., such as ≤475° C., ≤450° C., ≤425° C., or ≤400° C. A process may be conducted at temperatures of ≥200° C., such as ≥250° C., or ≥300° C. in the methylation reactor which has been found to provide commercially viable methylation reaction rates, for example methylation processes performed at a weight hourly space velocity of the combined feeds from 1 hour$^{-1}$ to 50 hour$^{-1}$. The process may be conducted at temperatures from 200° C. to 500° C., such as from 300° C. to 475° C., from 275° C. to 450° C., or from 250° C. to 400° C. Such low-temperature reaction can be particularly utilized when a MWW framework type zeolite is present in the methylation catalyst. Such low-temperature reaction can be particularly advantageous where a fixed bed of the methylation catalyst is present in the methylation reactor. The ability of the processes of this disclosure to be operated at low temperature carries many advantages, to name a few: higher energy efficiency, longer catalyst life, fewer species of byproducts, and small quantities of byproducts that otherwise would be produced at higher temperatures, compared to conventional benzene/toluene methylation processes operated at temperatures higher than 500° C.

WHSV values based on total aromatic hydrocarbon feed and methylating agent feed can range from, e.g., 0.5 hour$^{-1}$ to 50 hour$^{-1}$, such as from 5 hour$^{-1}$ to 15 hour$^{-1}$, from 1 hour$^{-1}$ to 10 hour$^{-1}$, from 5 hour$^{-1}$ to 10 hour$^{-1}$, or from 6.7 hour$^{-1}$ to 10 hour$^{-1}$. In some embodiments, at least part of the aromatic hydrocarbon feed, the methylating agent feed and/or the methylation product mixture effluent may be present in the methylation reactor in the liquid phase. As is described in more detail below, alteration of the WHSV may be desired as reaction temperature changes in order to maintain desired conversion of benzene, toluene, methanol, and/or dimethyl ether.

Catalysts used in chemical processes can experience a deactivation, i.e., reduction in catalytic activity. Thus, typically, at the start of a catalyst cycle when the catalyst is fresh, the catalyst has a high activity, resulting in a high conversion of reactants. Overtime, as the catalyst ages, it may be deactivated by, e.g., coke deposition on the catalyst. After a certain runtime, the activity of the catalyst may be reduced to such a low level that catalyst regeneration or change-out may be required. The deactivation of the catalyst over time can be characterized by the reduction of conversion of a particular reactant in the feed.

Thus, in a benzene/toluene methylation with methanol/DME process for making products such as xyplenes, the methylation catalyst, which may comprise a zeolite, typically experiences deactivation overtime. Such deactivation can be calculated as the reduction of conversion of toluene or benzene after a certain period of time while the methylation catalyst is on the stream. The period of time can be expressed as a cumulative quantity (grams) of total feed, including the aromatic hydrocarbon feed and the methylating agent feed, per gram of the methylation catalyst that the methylation catalyst has processed. Thus, in this disclosure, the deactivation rate (R(d)) of the methylation catalyst can be calculated as follows:

$$R(d) = \frac{C1 - C2}{C1 * W} \times 100\%$$

(gram methylation catalyst per gram of total feed)

where C1 is the conversion of toluene if the aromatic hydrocarbon feed comprises toluene at a first point of time during the catalyst cycle, and C2 is the conversion of toluene at a second point of time corresponding to immediately after an additional W grams of total feeds have been processed by a gram of the methylation catalyst, where W ≥2000. Likewise, where the aromatic hydrocarbon feed comprises benzene, the deactivation rate of the methylation catalyst can be calculated based on benzene conversion using the same formula, where C1 and C2 are benzene conversions, respectively, and W is the number of grams of total additional feeds processed in the time interval from the first point of time to the second point of time, and W ≥2000. Since the methylation catalyst can deactivate at a relatively low pace, a sufficiently large time interval corresponding to ≥2000 grams of total feeds processed per gram of the methylation catalyst is used in the above calculation.

The unit of the deactivation rate of the methylation catalyst calculated above is gram methylation catalyst per gram of total feed.

In the processes of this disclosure, due to the use an elevated reactor absolute pressure of ≥4300 kPa, the deactivation rate of the methylation catalyst was unexpectedly reduced. Thus, in certain embodiments the processes for converting benzene and/or toluene of this disclosure can exhibit a methylation deactivation rate R(d)≤0.005% (e.g., ≤0.004%, ≤0.003%, ≤0.002%, ≤0.001%) gram methylation catalyst per gram of total feed. The R(d) may be calculated based on toluene conversion if the aromatic hydrocarbon feed comprises toluene, or based on the benzene conversion if the aromatic hydrocarbon feed comprises benzene. Experiments below unexpectedly demonstrated such low methylation catalyst deactivation rate, which can be several times lower than a comparative process run under an absolute pressure in the methylation reactor <4300 kPa.

In certain embodiments where the aromatic hydrocarbon feed comprises toluene, after W1 mass units of the aromatic hydrocarbon feed and the methylating agent feed combined have been processed per mass unit of the methylation catalyst under an absolute pressure of at least 4300 kPa, where W1 ≥1,000, the conversion of toluene is c1; after W1+4,000 mass units of the aromatic hydrocarbon feed and the methylating agent feed combined have been processed per mass unit of the methylation catalyst under an absolute pressure of at least 4300 kPa, the conversion of toluene is c2; and c2/c1 ≥0.8. In certain further embodiments, after W1+6,000 mass units of the aromatic hydrocarbon feed and the methylating agent feed combined have been processed per mass unit of the methylation catalyst under an absolute pressure of at least 4300 kPa, the conversion of toluene is c3; and c3/c1 ≥0.8. In certain other embodiments, after W1+8,000 mass units of the aromatic hydrocarbon feed and the methylating agent feed combined have been processed per mass unit of the methylation catalyst under an absolute pressure of at least 4300 kPa, the conversion of toluene is c4; and c4/c1 ≥0.8. In certain embodiments, after W1+10,000 mass units of the aromatic hydrocarbon feed and the methylating agent feed combined have been processed per mass unit of the methylation catalyst under an absolute pressure of at least 4300 kPa, the conversion of toluene is c5; and c5/c1 ≥0.8. In certain embodiments, after W1+12,000 mass units of the aromatic hydrocarbon feed and the methylating agent feed combined have been processed per mass unit of the methylation catalyst under an absolute pressure of at least 4300 kPa, the conversion of toluene is c6; and c6/c1 ≥0.8.

The methylation reaction can be conducted in a methylation reactor, which can be any suitable reactor system including, but not limited to, a fixed bed reactor, a moving bed reactor, a fluidized bed reactor, and/or a reactive distillation unit. In addition, the methylation reactor may include a single methylation zone or multiple methylation zones located in the same or different reactors. A methylation reactor may include a bed of methylation catalyst particles disposed therein where the particles have insignificant motion in relation to the bed (a fixed bed). In addition, injection of the methylating agent feed can be effected at a single point in the methylation reactor or at multiple points spaced along the methylation reactor. The aromatic hydrocarbon feed and the methylating agent feed may be pre-mixed before entering the methylation reactor.

In certain embodiments of the this disclosure, the methylation reactor includes a single fixed bed or a plurality of fixed beds, continuous flow-type reactors in a down flow mode, where the reactors may be arranged in series or parallel. The methylation reactor may include a single or multiple catalyst beds in series and/or in parallel. The catalyst beds may have various configurations such as: a single bed, several horizontal beds, several parallel packed tubes, multiple beds each in its own reactor shell, or multiple beds within a single reactor shell. In certain embodiments, the fixed beds provide uniform flow distribution over the entire width and length of the bed to utilize substantially all of the methylation catalyst system. In at least one embodiment, the methylation reactor can provide heat transfer from a fixed bed to provide effective methods for controlling temperature.

The concentration of methylating agent feed can be adjusted by, e.g., staged additions thereof. By staged additions, aromatic hydrocarbon/methylating agent feed concentrations can be maintained at optimum levels for desirable benzene and/or toluene conversion. In at least one embodiment, the ratio of aromatic hydrocarbon feed to methylating agent feed is R(a/m) which is determined by the following equation:

$$R(a/m) = \frac{M(tol) + 2 \cdot M(bz)}{M(\text{methanol}) + 2 \cdot M(DME)}$$

Where M(tol) is the moles of toluene in the aromatic hydrocarbon feed, M(bz) is the moles of benzene in the aromatic hydrocarbon feed, M(methanol) is the moles of methanol in the methylating agent feed, and M(DME) is the moles of dimethyl ether in the methylating agent feed. In various embodiments, R(a/m) is ≥1, ≥2, or ≥2.5, and ≤6, ≤5, or ≤4, or ranges from 1 to 5 or from 2 to 4. For the purpose of producing xylenes, each benzene molecule needs to be methylated by two methanol molecules or one DME molecule, and each toluene by one methanol molecule or half a DME molecule. Over-methylation of benzene and/or toluene can result in the production undesirable C9+ aromatic hydrocarbons as byproducts. To prevent over-methylation, it is highly desirable that R(a/m) ≥1.5. Preferably 2≤R(a/m)≤5. More preferably 2≤R(a/m)≤4. The efficiency of the methylation process can be reduced at higher R(a/m), e.g., R(a/m) >5, due to large quantity of toluene/benzene present in the methylation reaction product mixture effluent, which needs to be separated and recycled to the methylation reactor.

The efficiency of a methylation reactor containing a fixed bed of methylation catalyst may be affected by the pressure drop across the fixed bed. The pressure drop depends on various factors such as the path length, the methylation catalyst particle size, and pore size. A pressure drop that is too large may cause channeling through the catalyst bed, and poor efficiency. In some embodiments, the methylation reactor has a cylindrical geometry with axial flows through the catalyst bed.

The various designs of the methylation reactor may accommodate control of specific process conditions, e.g. pressure, temperature, and WHSV. The WHSV determines volume and residence time that may provide the desired conversion.

The product of the methylation reaction (also referred to as the methylation product mixture effluent) can comprise: xylenes, benzene, and/or toluene (both residual and coproduced in the process), C9+ aromatic hydrocarbons, co-produced water, and unreacted methanol and DME. In some embodiments, the process is operated at sufficient WHSV so that only a portion of the methanol is reacted with the aromatic hydrocarbon feed and the methylation product mixture effluent contains residual methanol and/or DME.

The temperature of the methylation reactor may affect by-product formation and a temperature lower than 500° C. may decrease light gas formation. In some embodiments, the methylation product mixture effluent contains ≤10 wt %, such as ≤5 wt %, ≤2 wt %, ≤1 wt %, or is substantially free of light gases generated by methanol decomposition to ethylene or other olefins.

In some embodiments, the methylation product mixture effluent is separated into an aqueous phase and an oil phase. The method of separating the aqueous phase from the oil phase can be accomplished by a coalescing plate separator, e.g., described in U.S. Pat. Nos. 4,722,800 and 5,068,035; a centrifugal separator, e.g., described in U.S. Pat. Nos. 4,175,040; 4,959,158; and 5,591,340; a hydrocyclone separator, e.g., described in U.S. Pat. Nos. 4,428,839; 4,927,536; and 5,667,686; or other suitable methods. In some embodiments, the oil phase of the methylation product mixture effluent may contain at least 80 wt % xylenes. In some embodiments, the methylation product mixture effluent comprising an aqueous phase and an oil phase enters a first separation unit; the aqueous phase, which is denser, settles to the bottom of an upstream chamber and can be drawn from the water drain tube down below. The oil phase, which is lighter, is located on top of the aqueous phase and can spill over a dividing wall to the downstream chamber where it can then be drawn from the bottom of the downstream chamber.

After separation of the aqueous phase, the oil phase may be separated into a DME-rich stream, an aromatics-rich stream, and methane or other by-products. In some embodiments, the DME-rich stream may be fully or partially separated from other products and by-products to be recycled through a first recycling channel. In some embodiments, the DME-rich stream contains DME in ≥50 wt %, ≥60 wt %, ≥70 wt %, ≥80 wt %, ≥90 wt %, ≥95 wt %, ≥98 wt %, or ≥99 wt %, based on the total weight of the DME-rich stream. In some embodiments, the methylating agent feed contains DME from the is DME-rich stream in ≥20 wt %, ≥40 wt %, ≥60 wt %, ≥80 wt %, ≥90 wt %, ≥95 wt %, ≥98 wt %, or ≥99 wt %, based on the total weight of the DME in the methylating agent stream. In at least one embodiment all of the DME in the methylation agent feed is obtained from the DME-rich stream.

In some embodiments, methane is partially or fully separated from other products, and by-products. In at least one embodiment, the methane is used as fuel gas.

In some embodiments, the aromatics-rich stream comprises C6 to C9+ aromatic hydrocarbon products and by-products. In another embodiment, the aromatics-rich stream is further separated to produce a C9+ process stream containing C9+ aromatics. In at least one embodiment, the C9+ process stream can be recovered for blending into the gasoline pool or transalkylated with benzene and/or toluene to make additional xylenes. In some embodiments, the aromatics-rich stream comprises xylenes in ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream. In some embodiments, the aromatics-rich stream comprises p-xylene. In some embodiments, the aromatics-rich stream contains p-xylene in greater than ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream.

In some embodiments the DME-rich stream and the aromatics-rich stream are separated in a distillation system including one or more distillation columns. The distillation system may be operated at increased pressure, such as greater than ≥400 kPag, ≥500 kPag, ≥600 kPag, ≥700 kPag, ≥800 kPag, ≥900 kPag, such as from 400 kPag to 1400 kPag, from 600 kPag to 1300 kPag, from 700 kPag to 1200 kPag, from 800 kPag to 1100 kPag, or from 900 kPag to 1000 kPag.

In some embodiments, the aromatics-rich stream is further separated into a xylenes-rich stream and a toluene-rich stream, which may comprise benzene. The toluene-rich stream comprising benzene and/or toluene to be recycled through a second recycling channel may contain toluene in ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In another embodiment, the toluene-rich stream comprises benzene and toluene in a combined wt % of ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In some embodiments, the xylenes-rich stream contains an equilibrium mixture of ortho-, meta-, para-xylenes comprising about 24 wt % of p-xylene, about 50 wt % of meta-xylene, and about 26 wt % of ortho-xylene. The xylenes-rich stream may contain p-xylene in ≥10 wt %, ≥20 wt %, ≥30 wt %, ≥40 wt %, ≥50 wt %, ≥60 wt %, ≥70 wt %, or ≥80 wt %, based on the total weight of the xylenes-rich stream.

The xylenes-rich stream may be sent to a separation/recovery system to recover a high-purity p-xylene product and an optional o-xylene product. A xylenes loop can include a p-xylene recovery unit, such as a crystallization separation unit and/or an adsorptive chromatography separation unit known in the prior art. The p-xylene recovery unit can produce a high-purity p-xylene product and a p-xylene-deleted stream rich in o-xylene and m-xylene. The xylenes-loop can further include an isomerization unit such as a vapor-phase isomerization unit and/or a liquid phase isomerization unit known in the prior art to further convert a portion of the o-xylene and m-xylene in the p-xylene-depleted stream to p-xylene. The isomerized stream can be recycled to the p-xylene recovery unit in the xylenes loop to recover additional quantity of p-xylene.

In certain embodiments, the aqueous phase is separates a methanol-rich stream from a water-rich stream. In some embodiments, the methanol-rich stream contains methanol at >50 wt %, ≥60 wt %, ≥70 wt %, ≥80 wt %, ≥90 wt %, ≥95 wt %, ≥98 wt %, or ≥99 wt %, based the overall weight of the methanol-rich stream. In at least one embodiment, the methanol rich stream is recycled to the methylation agent feed or the methylation reactor. In some embodiments, the separation of the methanol-rich stream from the water-rich stream is accomplished by a distillation system; an example system is described in U.S. Pat. Nos. 3,293,154 and 4,210,495.

In another embodiment, the DME-rich stream is combined with the methanol-rich stream to form a single recycle stream. In another embodiment, the toluene-rich stream, the DME-rich stream, and the methanol-rich stream are combined to form a single recycle stream.

As another aspect of this disclosure, a process for converting for converting benzene and/or toluene, the process comprising: (a) feeding an aromatic hydrocarbon feed and a methylating agent feed into a methylation reactor, the aromatic hydrocarbon feed comprising benzene and/or toluene, and the methylating agent comprising methanol and/or dimethyl ether; (b) contacting the aromatic hydrocarbon feed with the methylating agent feed in the presence of a methylation catalyst in the methylation reactor under methylation reaction conditions comprising an absolute pressure in the methylation reactor of below 4300 kPa, to produce a methylation product mixture effluent comprising toluene, p-xylene, methanol, and dimethyl ether; and (c) increasing the absolute pressure in the methylation reactor to at least 4300 kPa.

As indicated above, at an absolute pressure in the methylation reactor <4300 kPa, e.g., the methylation catalyst can deactivate at a significantly higher rate than at a pressure ≥4300 kPa, e.g., ≥4500 kPa. At the beginning of a catalyst cycle, a methylation catalyst may have sufficiently high activity, and thus can run at pressure <4300 kPa efficiently and effectively. After a certain period of time on stream, as the catalyst has deactivated to a certain level, the reactor pressure may be ramped up to ≥4300 kPa to decrease the deactivation rate of the methylation catalyst, thereby extending the life cycle. As discussed above, after the pressure has been increased to ≥4300 kPa, the reactor pressure may be further increased overtime as well.

The Methylation Catalyst

Any suitable catalyst capable of catalyzing conversion of toluene and/or benzene to xylenes with methanol and/or DME can be used for the methylation processes of this disclosure. Examples of such catalysts are crystalline microporous materials such as zeolite-based, as well as non-zeolite-based, molecular sieves and can be of the large, medium, or small pore type. Molecular sieves can have 3-dimensional, four-connected framework structure of corner-sharing [TO$_4$] tetrahedra, where T can be a tetrahedrally coordinated atom. These molecular sieves are often described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al, *Introduction to Zeolite Science and Practice*, Second Completely Revised and Expanded Edition, Volume 137, pages 1-67, Elsevier Science, B.V., Amsterdam, Netherlands (2001). Another convenient measure of the extent to which a molecular sieve provides control of molecules of varying sizes to its internal structure is the Constraint Index. The method by which Constraint Index is determined is described fully in U.S. Pat. No. 4,016,218, which is incorporated herein by reference for details of the method.

Non-limiting examples of molecular sieves include small pore molecular sieves (e.g., AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof), medium pore molecular sieves (e.g., AFO, AEL, EUO, HEU, FER, MEL, MFI, MTW, MTT, TON, and substituted forms thereof), large pore molecular sieves (e.g., EMT, FAU, and substituted forms thereof), intergrowths thereof, and combinations thereof. Other molecular sieves include, but are not limited to, ANA, BEA, CFI, CLO, DON, GIS, LTL, MER, MOR, MWW, SOD, intergrowths thereof, and combinations thereof. In some embodiments, the molecular sieve has an MWW framework type (morphology).

The small, medium, and large pore molecular sieves have from a 4-ring to a 12-ring or greater framework-type. In some embodiments, the zeolitic molecular sieves have 6-, 8-, 10-, or 12-ring structures and an average pore size in the range from about 3 Å to 15 Å. In other embodiments, the molecular sieves are aluminosilicate molecular sieves and have a 6-ring or an 8-ring structure and an average pore size of about 5 Å or less, such as in the range from 3 Å to about 5 Å, for example from 3 Å to about 4.5 Å or from 3.5 Å to about 4.2 Å.

Other non-limiting examples of zeolitic and non-zeolitic molecular sieves include one or a combination of the following: Beta (U.S. Pat. No. 3,308,069 and Reissue No. 28,341), ZSM-3 (U.S. Pat. No. 3,415,736), ZSM-4 (U.S. Pat. No. 4,021,947), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-14 (U.S. Pat. No. 3,923,636), ZSM-18 (U.S. Pat. No. 3,950,496), ZSM-20 (U.S. Pat. No. 3,972,983), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245), ZSM-38, ZSM-48 (U.S. Pat. No. 4,397,827), ZSM-50, ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), ultrastable Y zeolite (USY) (U.S. Pat. Nos. 3,293,192 and 3,449,070), Dealuminized Y zeolite (Deal Y) (U.S. Pat. No. 3,442,795), mordenite (naturally occurring and synthetic) (for synthetic mordenite U.S. Pat. Nos. 3,766,093 and 3,894,104), SSZ-13, titanium aluminosilicates (TASOs) such as TASO-45 (European Patent No. EP-A-0 229 295), boron silicates (U.S. Pat. No. 4,254,297), titanium aluminophosphates (TAPOs) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), those disclosed in International Publication No. WO 98/57743 published Dec. 23, 1988 (molecular sieve and Fischer-Tropsch), those disclosed in U.S. Pat. No. 6,300,535 (MFI-bound zeolites), mesoporous molecular sieves (U.S. Pat. Nos. 6,284,696, 5,098,684, 5,102,643 and 5,108,725), and the like, and intergrowths and/or combinations thereof.

In an embodiment, the methylation catalyst comprises an aluminosilicate methylation catalyst. Aluminosilicates, as used herein, can include those having a molar relationship of $X_2O_3:(n)YO_2$ (wherein X is a trivalent element e.g. Al and Y is a tetravalent element e.g. Si), in which n≤500, such as ≤250, ≤100, such as from 30 to 100.

Non-limiting examples of trivalent X can include aluminum, boron, iron, indium, gallium, and combinations thereof. Non-limiting examples of tetravalent Y can include silicon, tin, titanium, germanium, and combinations thereof.

In embodiments where X represents aluminum and Y represents silicon, the factor n represents a silica:alumina molar ratio, also termed $Si:Al_2$. Another measure of relative proportion in such cases is the ratio of Y:X, or the silicon: aluminum ratio. In one embodiment, the silicon:aluminum (Si:Al) ratio of aluminosilicates is ≤500, such as ≤250, ≤100, or ≤50, such as from 1 to 50, from 5 to 50, or from 15 to 50.

Other non-limiting examples of aluminosilicate catalysts and compositions can be found, for instance, in U.S. Patent Application Publication No. 2003/0176751 and U.S. patent application Ser. No. 11/017,286 (filed Dec. 20, 2004) and 60/731,846 (filed Oct. 31, 2005).

One class of molecular sieve suitable for use in a process of this disclosure has a Constraint Index ≤5, and is crystalline microporous material of the MWW framework type. MWW framework type refers to a type of crystalline microporous material that comprises at least two independent sets of 10-membered ring channels and has composite building units of d6r (t-hpr) and mel as defined and discussed in *Compendium of Zeolite Framework Types. Building Schemes and Type Characteristics* Van Koningsveld, Henk, (Elsevier, Amsterdam, 2007), incorporated by reference. Crystalline microporous materials of the MWW framework type can include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system. Crystalline microporous materials of the MWW framework type include molecular sieves having natural tiling units of t-dac-1, t-euo, t-hpr, t-kah, t-kzd, t-mel, t-mww-1, t-mww-2, and t-srs as defined and discussed in *Three-periodic Nets and Tilings: Natural Tilings for Nets*, V. A. Blatov, O. Delgado-Friedrichs, M. O'Keeffe and D. M. Proserpio, Acta Crystallogr. A 63, 418-425 (2007), incorporated by reference.

In at least one embodiment, the crystalline microporous material is a zeolite. As used herein, the term "crystalline microporous material of the MWW framework type" comprises one or more of:

(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, incorporated herein by reference);

(b) molecular sieves made from a second degree building block, being a 2-dimensional tiling of such MWW framework topology unit cells, forming a monolayer of one unit cell thickness, in one embodiment, one c-unit cell thickness;

(c) molecular sieves made from common second degree building blocks, being layers of one or more than one unit cell thickness, where the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and (d) molecular sieves made by any regular or random 2-dimensional or 3-dimensional combination of unit cells having the MWW framework topology.

Examples of crystalline microporous materials of the MWW framework type include MCM-22 (U.S. Pat. No. 4,954,325), PSH-3 (U.S. Pat. No. 4,439,409), SSZ-25 (U.S. Pat. No. 4,826,667), ERB-1 (European Patent No. 0293032), ITQ-1 (U.S. Pat. No. 6,077,498), ITQ-2 (International Publication No. WO97/17290), MCM-36 (U.S. Pat. No. 5,250,277), MCM-49 (U.S. Pat. No. 5,236,575), MCM-56 (U.S. Pat. No. 5,362,697), UZM-8 (U.S. Pat. No. 6,756,030), UZM-8HS (U.S. Pat. No. 7,713,513), UZM-37 (U.S. Pat. No. 7,982,084), EMM-10 (U.S. Pat. No. 7,842,277), EMM-12 (U.S. Pat. No. 8,704,025), EMM-13 (U.S. Pat. No. 8,704,023), UCB-3 (U.S. Pat. No. 9,790,143B2), and mixtures thereof.

In some embodiments, the crystalline microporous material of the MWW framework type may be contaminated with other crystalline materials, such as ferrierite or quartz. These contaminants may be present in quantities of ≤10 wt %, such as ≤5 wt %.

In some embodiments, the molecular sieves are not subjected to pre-treatments, such as high temperature steaming, to modify their diffusion properties. In other embodiments, the molecular sieves may be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350° C. to 550° C. A suitable silica-selectivation procedure is described in U.S. Pat. No. 5,476,823. In another embodiment, the catalyst is selectivated by contacting the catalyst with steam. Steaming of the zeolite is effected at a temperature of ≥950° C., such as from 950° C. to 1075° C., or from 1000° C. to 1050° C., for 10 minutes to 10 hours, such as from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026. In some embodiments, a combination of silica selectivation, steam selectivation, and/or coke selectivation may be employed.

It may be desirable to combine the molecular sieve, prior to selectivating, with at least one oxide modifier, such as at least one oxide selected from elements of Groups 2 to 4 and 13 to 16 of the Periodic Table. In at least one embodiment, the oxide modifier is an auxiliary catalyst. In some embodiments, the oxide modifier is selected from oxides of boron, magnesium, calcium, lanthanum, and phosphorus. In some cases, the molecular sieve may be combined with more than one oxide modifier, for example a combination of oxides of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be from 0.05 wt % and 20 wt %, such as from 0.1 wt % to 10 wt %, based on the weight of the final catalyst. Where the modifier comprises phosphorus, incorporation of modifier into the catalyst is conveniently achieved by the methods described in U.S. Pat. Nos. 4,356,338; 5,110,776; 5,231,064; and 5,348,643.

The molecular sieves may be used as the methylation catalyst without any binder or matrix, in a self-bound form. Alternatively, the molecular sieves may be composited with another material which is resistant to the temperatures and other conditions employed in the methylation reaction. Such binder or matrix materials can include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve whether combined therewith or present during its synthesis, which itself is catalytically active may be termed an auxiliary catalyst. Inactive materials suitably serve as diluents to control the amount of conversion so that products may be obtained economically and orderly without employing other means for controlling the rate of reaction. These materials may be incorporated into naturally occurring clays, for example, bentonite and kaolin, to improve the crush strength of the catalyst under commercial operating conditions and function as binders or matrices for the catalyst. The relative proportions of molecular sieve and auxiliary catalyst vary widely, with the sieve content ranging from 1 wt % to 90 wt %, and in some embodiments the composite is prepared in the form of beads, in the range of 2 wt % to 80 wt % of the composite.

FIG. 1 schematically illustrates a process for converting benzene and/or toluene via methylation with methanol and/or DME to produce p-xylene according to at an embodiment of this disclosure. Methylating agent feed 101, comprising methanol and/or DME is combined with aromatic hydrocarbon feed 103 comprising toluene and/or benzene in fluid transfer line 105. Fluid transfer line 105 may contain an agitator or other mixing device (not shown) in order to combine methylating agent feed 101 and aromatic hydrocarbon feed 103 to form a combined feed. The combined feed is fed by line 107 to heat exchanger 109 to pre-heat the combined feed. The heated combined feed comprising a mixture of feed 101 and feed 103 is fed through line 111 to heat exchanger 113. Heat exchanger 113 may be used to heat or cool the combined feed as necessary. The combined feed is then passed through line 115, through inlet 117 to methylation reactor 119. Line 115 may also include a pump or series of pumps (not shown) in order to maintain sufficient pressure and WHSV in methylation reactor 119. Inlet 117 may accept one or more feeds or streams comprising one or more recycle channels. Methylation reactor 119 can be a fixed or fluid bed reactor containing the methylation catalyst (not shown) and auxiliary catalyst (not shown) and is operated at methylation reaction conditions, which may include temperatures less than 500° C. and pressures greater than 100 kPa. Methylation reactor 119 may have one or more methylation reactors (not shown) where the methylation catalyst and auxiliary catalyst are present. The product of the methylation conditions in the methylation reactor (the methylation product mixture effluent) can be a mixture of xylenes, water, methanol, dimethyl ether, and by-products and is fed from methylation reactor 119 through outlet 121 to line 123 and ultimately to heat exchanger 109 to be cooled. The cooled methylation product mixture effluent is passed through line 125 to heat exchanger 127 to be either heated or cooled as necessary to arrive at the desired temperature for separation, then through line 129 to separation subsystem 131. Separation subsystem 131 may contain one or more separation units (not shown). Separation subsystem 131 may separate methane or other light gases which can be removed via line 133 and may be used as fuel gas (not shown).

Separation subsystem 131 may further separate a dimethyl ether-rich stream which is then provided to line 135, which can be recycled into methylating agent feed 101 or methylation reactor inlet 117. Line 135 may include pumps or compressors so that the DME-rich stream may enter the methylation agent feed or methylation reactor at a desired pressure, the combination of lines and pumps or compressors is a first recycling channel. The first recycling channel, may contain other combinations of lines and pumps or compressors (not shown) suitable to recycle DME to methylation reactor 119.

Separation subsystem 131 may further separate toluene-rich stream 137, which may contain benzene and can be recycled into aromatic hydrocarbon feed 103 or methylation reactor inlet 117. Line 137 may include pumps or compressors so that the toluene-rich stream may enter the aromatic hydrocarbon feed or methylation reactor at a desired pressure; the combination of lines and pumps or compressors is a second recycling channel. Furthermore, the separation may yield a xylenes-rich stream which is sent out of line 139, and line 139 may be connected to other systems for further processing (not shown). The xylenes-rich stream can be fed to a separation system such as a crystallizer or a simulated moving bed adsorption chromatography to recover a high-purity p-xylene product and produce a p-xylene-depleted stream. The p-xylene-depleted stream can be isomerized in an isomerization reactor in the presence of an isomerization catalyst to produce additional p-xylene.

Separation subsystem 131 may further separate a methanol-rich stream which is then provided to line 141, which can be recycled into methylating agent feed 101 or methylation reactor inlet 117. Line 141 may include pumps or compressors so that the methanol-rich stream may enter the methylation agent feed or methylation reactor at a desired pressure; the combination of lines and pumps or compressors is a third recycling channel. The third recycling channel, may contain other combinations of lines and pumps or compressors (not shown) suitable to recycle methanol to methylation reactor 119. Furthermore, the separation may yield a water-rich stream which is sent out of line 143, and line 143 may be connected to other systems for further processing (not shown), including wastewater purification systems (not shown).

EXAMPLES

Part A: Preparation of Methylation Catalyst

Example A1: Preparation of a MCM-49 Molecular Sieve Catalyst

MCM-49 crystals were fabricated pursuant to the teaching in U.S. Pat. No. 5,236,575. A MCM-49 methylation catalyst comprising an alumina binder was made from a mixture of MCM-49 crystals (before calcination) and high surface area (having a specific area ≥250 m$^2$/g) alumina (80:20 weight ratio) that was combined in a mulling operation. A mixture of MCM-49, high surface area alumina, and water was extruded into 1/20" Quadra-lobes and then dried in oven at 121° C. overnight. The dried extrudate was calcined in nitrogen (N2) at 538° C. to decompose and remove the organic template, used in the synthesis of MCM-49 crystals. The thus calcined extrudate was then humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. overnight and then calcined in air at 538° C. to obtain an H-form MCM-49 zeolite methylation catalyst composition. The H-formed extrudate was measured to have a total surface area of 536 m$^2$/g, which includes a mesopore area of 184 m2/g, and a collidine adsorption of ~71 μmoles/g. The alumina supported MCM-49 methylation catalyst was grinded to smaller particles and then sieved. Particles with 60/100 mesh sizes were used in the reactor runs as a comparative methylation catalyst system without an auxiliary catalyst, and was used to make the inventive methylation catalyst system of Example A2 below.

Part B: Toluene Methylation with Methanol Processes

The MCM-49 zeolite methylation catalyst prepared in Example A1 was then tested for their performances in a toluene methylation with methanol process in this Example A1.

A sample of the MCM-49 zeolite methylation catalyst prepared in Example A1 was loaded into a down flow fixed-bed steel reactor. A feed consisting of toluene and methanol at a toluene/methanol molar ratio of 3:1 was fed into the reactor. Reaction temperature was controlled at 350° C. and WHSV was controlled at 6.21 hr$^{-1}$. WHSV is defined as the ratio of the flow rate of the toluene/methanol feed to the weight of the alumina supported MCM-49 zeolite methylation catalyst. All reactor runs were performed under the same reaction conditions except pressure.

The composition of the methylation product mixture effluent was analyzed by a gas chromatograph, equipped with a flame ionization detector. Toluene conversion and para-xylene selectivity were calculated from the gas chromatography analysis. Toluene conversion is defined as the change in toluene concentration between the feed and product, normalized by the toluene concentration in the feed. Para-xylene selectivity is defined as the para-xylene concentration in the $C_8$ fraction of the methylation product mixture effluent. All calculations were made on molar basis.

Example B1 (Inventive): Toluene Methylation with Methanol Using the Methylation Catalyst of Example A1 at 675 Psig (4650 kPa, Gauge Pressure)

In this inventive example, the reactor pressure was set at 4650 kPa, gauge.

Example B2 (Comparative): Toluene Methylation with Methanol Using the Methylation Catalyst of Example A1 at 600 Psig (4140 kPa, Gauge Pressure)

In this comparative example, the reactor pressure was set at 4140 kPa, gauge.

Figure 2:
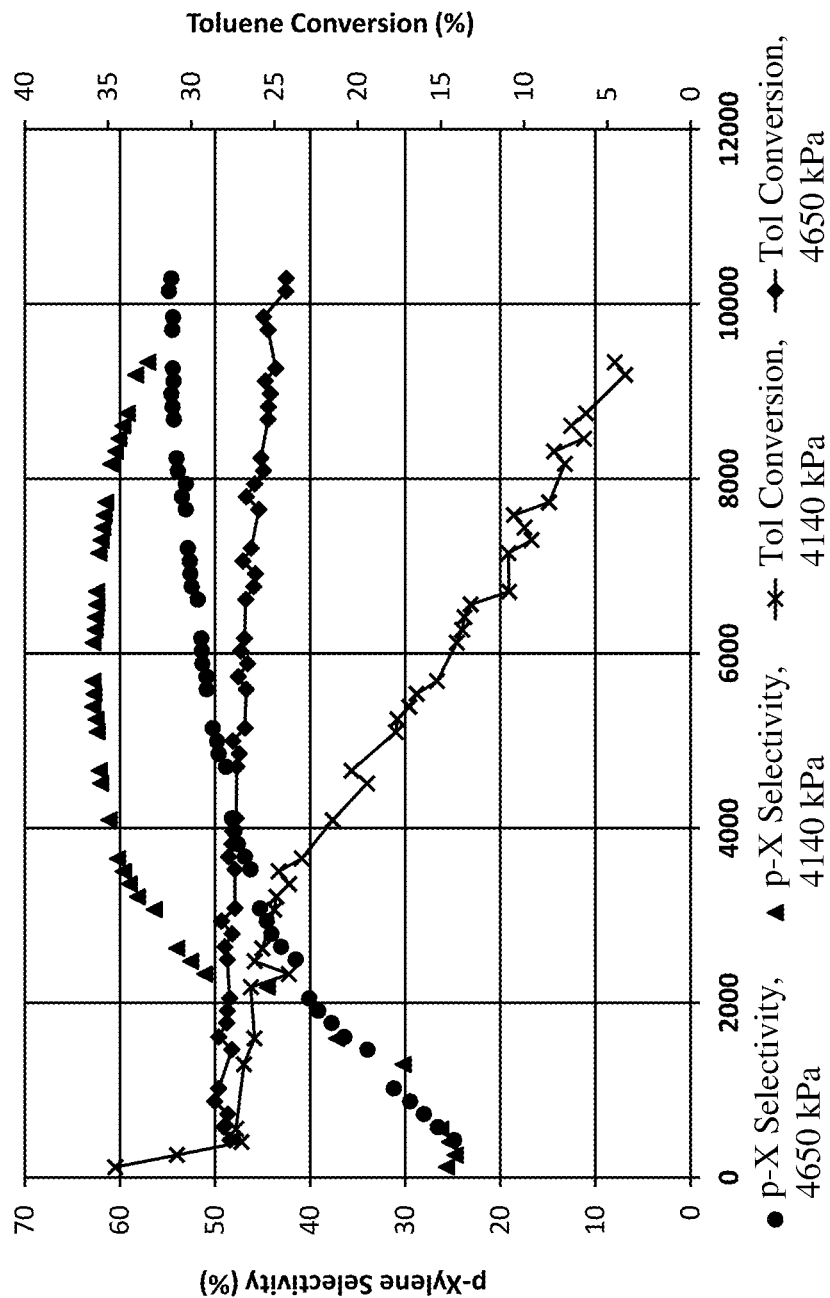
FIG. 2 is graph showing toluene conversion and p-xylene selectivity as a function of accumulative quantity of feeds (grams) per grams of methylation catalyst in exemplary processes of this disclosure for converting toluene via methylation with methanol.

Experiment data from the processes in Examples B1 and B2 are presented in FIG. 2. In FIG. 2, p-Xylene selectivity and methanol conversion are shown on the y-axes, and cumulative grams of feed per gram of catalyst are shown on the x-axis. FIG. 2 shows that the comparative process in Example B2 at a lower pressure had slightly higher p-xylene selectivity than the inventive process in Example B1. However, in terms of toluene conversion, in the comparative Example B2, toluene conversion was 27% at 430 grams of cumulative feed per gram of methylation catalyst, and 5% at 9330 grams of cumulative feed per gram of methylation catalyst. The deactivation rate is calculated as (27−5)/27/(9330−430)*100%=0.0092% gram of catalyst per gram of feed. In the inventive Example B1, toluene conversion was 28% at 430 grams of cumulative feed per gram of methylation catalyst, and 24% at 10300 grams of cumulative feed per gram of methylation catalyst. The deactivation rate is calculated as (28−24)/28/(10330−430)*100%=0.0014% gram of catalyst per gram of feed, which is merely 15% of the deactivation rate in the process of Example B2.

Overall, it has been found that increased pressure in a methylation reactor can suppress catalyst deactivation in processes for methylation of benzene and/or toluene with methanol and/or dimethyl ether to produce p-xylene. Suppression of deactivation of methylation catalysts improves catalyst utilization between regeneration cycles, which decreases cost of production. At lower methylation reactor pressures, more frequent catalyst regeneration processes may otherwise be required. The use of increased pressure within a methylation reactor can decrease the overall cost of p-xylene production by increasing the catalyst life cycle and decreasing the frequency of catalyst regenerations, which also reduces the frequency of reactor shut-downs which otherwise interrupt p-xylene production.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A process for converting benzene and/or toluene, the process comprising:
   (a) feeding an aromatic hydrocarbon feed and a methylating agent feed into a methylation reactor, the aromatic hydrocarbon feed comprising benzene and/or toluene, and the methylating agent comprising methanol and/or dimethyl ether; and
   (b) contacting the aromatic hydrocarbon feed with the methylating agent feed in the presence of a methylation catalyst comprising a zeolite of the MWW framework type in the methylation reactor under methylation reaction conditions comprising an absolute pressure of at least 4400 kPa, to produce a methylation product mixture effluent comprising toluene, p-xylene, methanol, and dimethyl ether.

2. The process of claim 1, wherein methylation conditions comprise an absolute pressure in the methylation reactor ranging from 4650 kPa to 8500 kPa.

3. The process of claim 1, wherein the methylation conditions comprise increasing the pressure in the reactor over time.

4. The process of claim 1, wherein the methylation catalyst has a deactivation rate less than 0.005% per (gram of feed per gram of catalyst).

5. The process of claim 1, wherein the methylation catalyst has a deactivation rate less than 0.003% per (gram of feed per gram of catalyst).

6. The process of claim 1, wherein:
   the aromatic hydrocarbon feed comprises toluene;
   after W1 mass units of the aromatic hydrocarbon feed and the methylating agent feed combined have been processed per mass unit of the methylation catalyst under the absolute pressure of at least 4400 kPa, where $W1 \geq 1,000$, the conversion of toluene is c1;
   after W1+4,000 mass units of the aromatic hydrocarbon feed and the methylating agent feed combined have been processed per mass unit of the methylation catalyst under the absolute pressure of at least 4400 kPa, the conversion of toluene is c2; and
   $c2/c1 \geq 0.8$.

7. The process of claim 6, wherein:
   after W1+8,000 mass units of the aromatic hydrocarbon feed and the methylating agent feed combined have been processed per mass unit of the methylation catalyst under the absolute pressure of at least 4400 kPa, the conversion of toluene is c3; and
   $c3/c1 \geq 0.8$.

8. The process of claim 1, wherein the methylation product mixture effluent comprises p-xylene at a concentration of greater than 30%, based on the total weight of all xylenes in the methylation product mixture effluent.

9. The process of claim 1, wherein in (a), the methylation catalyst is present in the methylation reactor in a fixed bed.

10. The process of claim 1, wherein in (b), the methylation reaction conditions comprise a temperature in a range from 200 to 500° C.

11. The process of claim 1, wherein the molar ratio of the aromatic hydrocarbon feed to the methylating agent feed is R(a/m), wherein $$R(a/m) = \frac{M(tol) + 2 \cdot M(bz)}{M(\text{methanol}) + 2 \cdot M(DME)}$$

where M(tol) and M(bz) are the moles of toluene and benzene in the aromatic hydrocarbon feed, respectively, and M(methanol) and M(DME) are the moles of methanol and dimethyl ether in the methylating agent feed, respectively, and wherein $1 \leq R(a/m) \leq 5$.

12. The process of claim 11, wherein $2 \leq R(a/m) \leq 4$.

13. The process of claim 1, wherein in (b), the methylation reaction conditions comprise a weight hourly space velocity in a range from 5 to 10 hour$^{-1}$, based on the total flow rate of the aromatic hydrocarbon feed and the methylating agent feed.

14. The process of claim 1, wherein the methylation product mixture effluent further comprises methanol and dimethyl ether, and the process further comprises:
   (c) obtaining a dimethyl ether-rich stream from at least a portion of the methylation product mixture effluent; and
   (d) recycling at least a portion of the dimethyl ether-rich stream obtained in (c) to (a) as at least a portion of the methylating agent feed.

15. The process of claim 14, wherein all of the dimethyl ether contained in the methylating agent feed in (a), if any, is the dimethyl ether recycled in (d) to (a).

16. The process of claim 14, wherein (c) comprises:
   (c1) separating the methylation product mixture effluent to obtain an aqueous phase and a hydrocarbon phase; and
   (c2) separating the hydrocarbon phase to obtain the dimethyl ether-rich stream of (c) and an aromatics-rich stream.

17. The process of claim 16, wherein (c) further comprises:
   (c3) separating the aromatics-rich stream to obtain a toluene-rich stream and a xylenes-rich stream; and
   (c4) recycling at least a portion of the toluene-rich stream obtained in (e) to (a) as at least a portion of the aromatic hydrocarbon feed.

18. The process of claim 16, wherein (c) further comprises:
   (c5) distilling the aqueous phase obtained in (c1) to obtain a methanol-rich stream and a water-rich stream; and
   (c6) recycling at least a portion of the methanol-rich stream obtained in (c5) to (a) as at least a portion of the methylating agent feed.

19. The process of claim 1, wherein the aromatic hydrocarbon feed comprises at least 90 wt % of toluene, based on the total weight of the aromatic hydrocarbon feed.

20. The process of claim 1, wherein the methylation catalyst comprises a zeolite, and wherein the zeolite is selected from MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, UCB-3, and mixtures of two or more thereof.

21. The process of claim 1, wherein methylation conditions comprise an absolute pressure in the methylation reactor of at least 4700 kPa.

22. The process of claim 1, wherein methylation conditions comprise an absolute pressure in the methylation reactor of at least 4600 kPa.

23. A process for converting benzene and/or toluene, the process comprising contacting an aromatic hydrocarbon feed and a methylating agent feed in a methylation reactor in the presence of a methylation catalyst comprising a zeolite of the MWW framework type under methylation reaction conditions to produce a methylation product mixture effluent, wherein the aromatic hydrocarbon feed comprises benzene and/or toluene, the methylating agent feed comprises methanol and/or dimethyl ether, and the methylation conditions comprise an absolute pressure of from 4650 kPa to 8500 kPa and a temperature of from 200 to 500° C.

24. The process of claim 23, wherein the methylation catalyst zeolite comprises MCM-49.

25. A process for converting for converting benzene and/or toluene, the process comprising:
   (a) feeding an aromatic hydrocarbon feed and a methylating agent feed into a methylation reactor, the aromatic hydrocarbon feed comprising benzene and/or toluene, and the methylating agent comprising methanol and/or dimethyl ether;
   (b) contacting the aromatic hydrocarbon feed with the methylating agent feed in the presence of a methylation catalyst comprising a zeolite of the MWW framework type in the methylation reactor under methylation reaction conditions comprising an absolute pressure in the methylation reactor of below 4300 kPa, to produce a methylation product mixture effluent comprising toluene, p-xylene, methanol, and dimethyl ether; and
   (c) increasing the absolute pressure in the methylation reactor to at least 4400 kPa.

26. The process of claim 1, wherein:
   the aromatic hydrocarbon feed comprises toluene,
   the methylating agent comprises methanol,
   the methylation conditions comprise an absolute pressure in the methylation reactor ranging from 4500 kPa to 8500 kPa, a temperature in a range from 250 to 450° C., and a weight hourly space velocity in a range from 5 to 10 hour$^{-1}$, based on the total flow rate of the aromatic hydrocarbon feed and the methylating agent feed, and
   the methylation catalyst has a deactivation rate less than 0.005% per (gram of feed per gram of catalyst).

27. The process of claim 26, wherein the zeolite comprises MCM-49.

* * * * *